United States Patent [19]

Schulz, Jr.

[11] 4,446,725

[45] May 8, 1984

[54] VOLUMETRIC ANALYSIS DEVICE FOR DETERMINING THE DRY RUBBER CONTENT OF LATEX

[76] Inventor: Frank C. Schulz, Jr., Cooper Hill, North Creek, N.Y. 12853

[21] Appl. No.: 382,044

[22] Filed: May 25, 1982

[51] Int. Cl.³ .............................................. G01N 15/06
[52] U.S. Cl. ...................................... 73/61 R; 73/149
[58] Field of Search ................. 73/49.4, 53, 61 R, 149; 210/86

[56] References Cited

U.S. PATENT DOCUMENTS

| | | |
|---|---|---|
| 2,296,852 | 9/1942 | Horner . |
| 2,325,026 | 7/1943 | Anway . |
| 2,325,027 | 7/1943 | Anway . |
| 2,327,642 | 8/1943 | Horner . |
| 2,482,147 | 9/1949 | Bashore . |
| 2,691,298 | 10/1954 | Cook ......................................... 73/61 |
| 3,160,000 | 12/1964 | Mosher ................. 73/61 R |
| 3,199,341 | 8/1965 | Heuer, Jr. et al. . |

FOREIGN PATENT DOCUMENTS 877337  10/1981  U.S.S.R. ................................. 73/149

Primary Examiner—Gerald Goldberg
Assistant Examiner—Joseph W. Roskos
Attorney, Agent, or Firm—David H. Semmes; Warren E. Olsen

[57] ABSTRACT

Determination of "dry rubber content" (DRC) within a latex solution. Particularly, a volumetric analysis device, including an elongated chamber with a removable filter cap positioned at one end. A compression plunger is mounted within the chamber upon one end of an axially reciprocable shaft. A compression handle and dial drum scale are mounted at that other end of the shaft, which extends through the chamber end wall. A liquid flocculating agent is mixed with a measured volume of latex solution within the chamber, then compressed by actuating the plunger. During compression, the liquid residue is urged through the filter cap. The remaining batch of precipitated latex is measured as the "dry rubber content", accordingly as the exterior dial drum intersects a reference scale on the cylinder interior.

8 Claims, 4 Drawing Figures

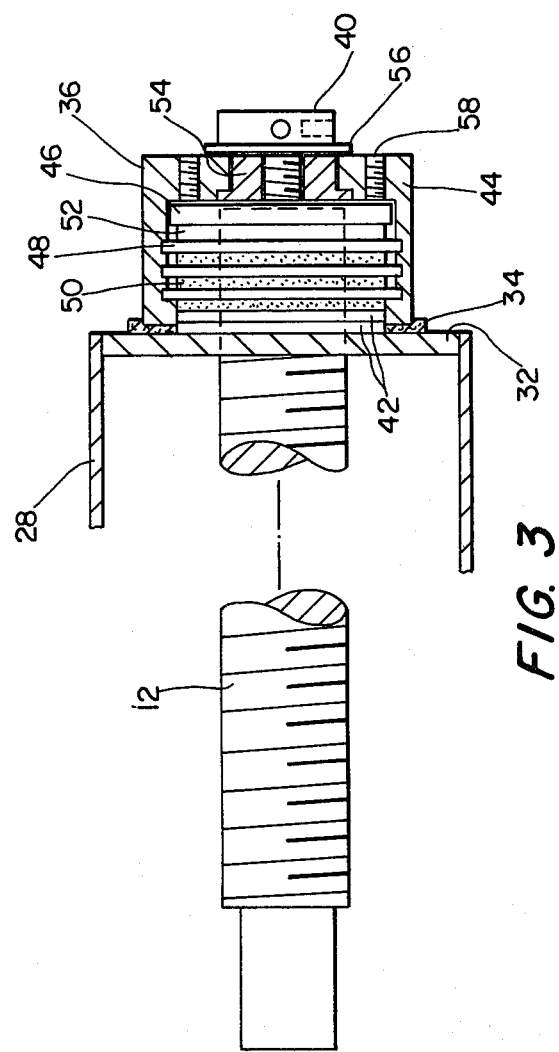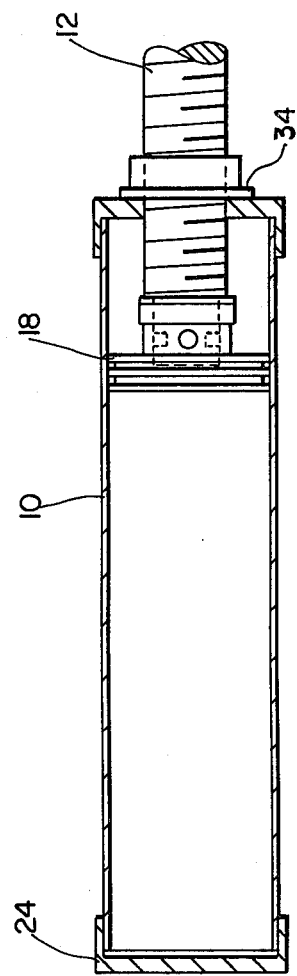

VOLUMETRIC ANALYSIS DEVICE FOR DETERMINING THE DRY RUBBER CONTENT OF LATEX

BACKGROUND OF THE INVENTION (1) Field of the Invention

Determination of the dry rubber content (DRC) in a precipitated latex solution.

*Hevea brasiliensis* is a biological product of very complex composition. Besides rubber hydrocarbon, it contains many proteinous and resinous substances, carbohydrates, inorganic matter and water. The following figures are typical for a freshly tapped sample of natural rubber latex:

|  | % |
|---|---|
| Total solids content | 22–48 |
| Dry rubber cement | 20–45 |
| Proteinous substances | 1.5 |
| Resinous substances | 2 |
| Carbohydrates | 1 |
| Inorganic matter | 0.5 |

The dry rubber content (DRC) of field latex, like other chemical compounds of the latex, varies according to season, weather, soil condition, clone, stimulation program and tapping system, etc. Dilution of the latex with water or preservatives also alters the DRC. The DRC of field latex normally falls in the range of 20–45% and 35% is generally taken as the average figure for plantation field latex.

(2) Description of the Prior Art

Prior art methods of determining DRC in a latex composition include:

(A) The Standard Laboratory Method

Based on Malyasian Standard MS 3:35:1975, wherein the known weight of field latex is acid coagulated and the wet latex coagulant is dried overnight in an oven at 70° C. before reweighing.

(B) The "Chee" Method

A simplified version of the Standard Laboratory Method, using a calibrated dipper and a simple balance for weighing the dried test piece. A kerosene oven may be used.

(C) The Hydrometric Method

Mixing one part of field latex with two parts of water and reading the specific gravity of the resultant mixture, using a latex hydrometer.

A description of the foregoing techniques appears in "Dry Rubber Content Determination Competition", undated, (Malaysian Rubber Research Development Board, Natural Rubber Building, 150 Jalan Ampang, Kuala Lumpur, Malaysia).

Prior art searching has developed:
HORNER U.S. Pat. No. 2,296,852
ANWAY U.S. Pat. No. 2,325,026
ANWAY U.S. Pat. No. 2,325,027
HORNER U.S. Pat. No. 2,327,642
BASHORE U.S. Pat. No. 2,482,147
COOK U.S. Pat. No. 2,691,298
HEUER, JR., et al. U.S. Pat. No. 3,199,341

These patents are discussed in a separate Prior Art Statement.

SUMMARY OF INVENTION

According to the present invention, the latex solution is treated with a liquid flocculating agent so as to produce natural rubber particulation. Then, a measured amount of the solution is introduced into the dry rubber content (DRC) determinator which is in the form of an elongated chamber, having a removable filter cap positioned at one end. A compression plunger is mounted upon an axial shaft which is reciprocably positioned within the cylinder. The cylinder includes an exterior reference scale and a dial drum affixed to a portion of the shaft extending through the other end of the chamber. The compression plunger may be urged to compress the measured batch of precipitated latex solution contained within the cylinder, while urging liquid residue through the filter cap. Thus, the determinator measures the DRC, as the volume of precipitated latex, per unit sample of solution. A standard of compression may be prefixed upon the exterior reference scale, so as to eliminate operator error. In addition, the scale may be calibrated for standard resiliency of natural latex in dynes/cc.

DESCRIPTION OF THE DRAWINGS

FIG. 3 is a fragmentary vertical section taken through the closed end of the cylinder, showing the clutch mechanism.

FIG. 4 is a fragmentary side elevation partially in section, showing the elongated chamber with the axial shaft and compression chamber in retracted position, prior to introducing the precipitated latex solution.

DESCRIPTION OF THE PREFERRED EMBODIMENTS

Figures 1, 2:
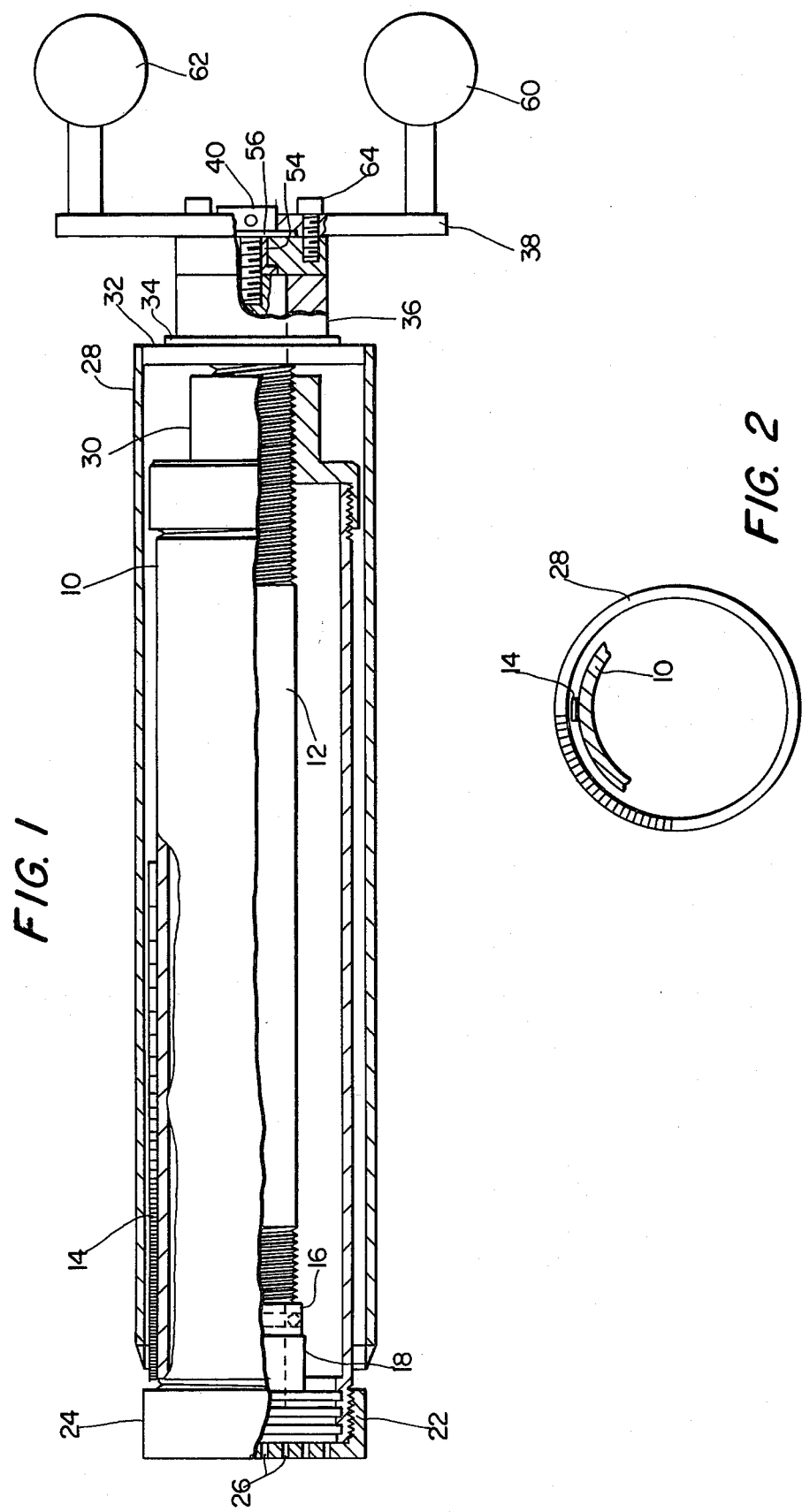
FIG. 1 is a side elevation, partially in section, showing the elongated chamber, with the axial shaft and compression plunger in fully compressed position, such that the plunger abuts the filter cap.
FIG. 2 is an end elevation, showing superpositioning of the dial drum with respect to the exterior reference scale and the cylinder exterior.

In FIG. 1 there is illustrated a volumetric analysis cylinder 10, having a removable filter cap 24, which supports inner screen filter 22 in juxtaposition with axially extending micropore outlets 26.

Pressure plunger 18, which may be formed from a soft plastic product, such as that trademarked "Teflon" and manufactured by E.I. DuPont de Nemours, may be secured to an axially extending feed screw shaft 12 by means of thrust bearing 16 or the like. Feed screw shaft 12 may have a feed shaft cap 30 and extend outwardly of cylinder 10, so as to engage drive clutch assembly 36. A felt shield 34 may be interposed between the drive clutch housing 44 and dial drum assembly 28, which encircles cylinder 10 and is coextensive therewith. Dial drum 28 may include a plurality of graduated markings, for example, 100 markings in the 360° area, as illustrated in FIG. 2. Longitudinal reference scale 14 may be positioned upon the exterior of cylinder 10, such that the bottom edge or open end of the dial drum 22 intercepts a milliliter reading upon scale 14, as compression of the latex composition is completed. A handle 38, including knobs 60, 62 may be secured to the drive clutch assembly by means of conventional bolts 64. A shaft lock screw 40 may be employed to secure the clutch assembly housing 36 to drive shaft 12.

As illustrated in FIG. 3, a washer may be interposed between the lockscrew 40 and the housing 36. A pair of pressure plates 42 may abut the dial drum 28 at the open end of clutch drive cover 44. Drive plate 48, and shaft pads 50, encircle the end of shaft 12 within housing 44. A slip pad 52 may abut clamp pad 46 adjacent bearing 54. A plurality of set screws 58 may engage clamp pad 46.

Current methods for determining the Dry Rubber Content (DRC") of *Hevea brasiliensis* either by laboratory analysis, the "Chee" Method or hydrometric analysis, fail to meet either the degree of accuracy or time requirement that can be met by using the present invention, together with standard volumetric methods for determining the volume of precipitated coagulate per unit volume of solution in a given sample.

The suggested test instrument will accurately measure the volume of precipitated latex per unit sample of solution, using a standard of compression that is prefixed upon reference scale 14, so as to eliminate operator error. Reference scale 14 is calibrated for the standard resiliency of natural latex in dynes/cc and is unalterable in the field.

The reference scale is read by the operator and is external to the compression of the latex within the cylinder.

The instrument is adjusted to read within 0.1541% within the 20 to 45% range for DRC of field latex inclusive of proteinous, resinous and other inorganic matter common in field latex to a total of 5% of the total sample.

Together with each instrument there may be provided a Data Table (see below), which is easily read and is descriptive of the analysis of the sample. These results are obtainable within two minutes.

CLUTCH DRIVE

1. Turning handle 38 drives feed screw shaft 12 through clutch assembly 36.

2. When selected pressure against plunger 18 has been achieved, shaft pads 50 allow slippage of drive plates 48 to occur. Drive plates 48 are keyed to clutch housing cover 44 by 0.060" radius tabs. Shaft pads 50 are keyed to drive shaft 12.

3. Slippage between shaft pads 50 and drive plates 48 is established through pressure against clamp pad 46 by means of set screws 58.

4. Adjustment of set screws 58 may be made only after removal of handle 38 from clutch housing 44.

5. When pressure against pressure plunger 18 becomes greater, than the friction of the clutch setting, dial drum 28 will rotate around cylinder 10, but will not advance along reference scale 14.

6. Drive clutch 36 and dial drum 28 rotate about bearing surfaces on feed screw shaft 12.

DETERMINATION OF DRY RUBBER CONTENT (DRC)

1. Coagulation precipitation of the solids in field latex solution may take place within volumetric steel cylinder 10.

2. The standard measured volume of latex is taken with a conventional "Teflon" beaker of 250 ml. Total capacity ±0.05%.

3. This volume is mixed with 250 ml of precipitating coagulant solution within cylinder 10 to a total volume of 500 ml. ±0.05%.

4. Filter cap 24 is secured upon cylinder 10, which is shaken, and torque handle 38 is turned by means of knobs 60, 62 until no further compression of the latex batch is possible.

5. The reading of dial drum 28 open end on reference scale 14 is taken to 1 mm and the corresponding values found in Data Table I, below.

6. Data Table I is based upon statistical data for natural latex and is within proscribed limits. The total extraneous solids should not exceed 5% of the total sample or 12.5 ml (6.16 mm) of the adjusted gross sample. Data Table I reflects this total of 5% extraneous solids, and represents only 5% for the total 250 ml sample. Consistency is repeatable for each sample and therefore corrected in each reading in the Data Table. Since the instrument reads to 1 mm (2.0922 ml), this is an error of only 0.008 or 0.1% for the 12.5 ml of the 250 ml sample. The Data Table reflects the DRC value, as corrected for both extraneous solids (5% maximum) per sample and 0.1% for total analysis.

ADVANTAGES OF INSTRUMENT

Spurious additives would have to be added in such great quantity that the percentage of volume would immediately reflect adulteration of the sample being tested. The allowable 5% on which each and every sample is evaluated then becomes a standard, not to be exceeded. Such samples would be rejected or, if desired, retested.

Excessive water, dilution, or other materials added that would affect density in hydrometric analysis have no effect upon this method.

Results are reproducible within limits established and do not vary from sample to sample, since the instrument is calibrated to read within 0.2% of the test DRC sample.

The instrument is mechanical and does not require electricity. The suggested acid coagulation solution is safe and nontoxic. The instrument will give results for all types of *Hevea brasiliensis*.

The test is easily performed by anyone. The scale is marked upon the instrument and once the reading is taken from the instrument, the operator reads the DRC value directly from the accompanying Data Table.

Accuracy of the precipitated floc is protected by an especial precipitating acid solution. The use of unqualified acid reagents could and most likely would produce entrapment of non-compressible liquid fractions in the compression chamber. This would be immediately noticed by a reading far greater than possible for normal latex.

DATA PROVIDED IN DATA TABLE I a. Readings in mm
b. Volume
c. Total percent of solids
d. Extraneous solids
e. DRC in percent of sample

DATA TABLE I

| READING IN MM | VOLUME | TOTAL SOLIDS | EXTRANEOUS SOLIDS | DRC % |
|---|---|---|---|---|
| 1 | 2.09221 | .836883 | .10461 | .795039 |
| 2 | 4.18441 | 1.67377 | .209221 | 1.59008 |
| 3 | 6.27662 | 2.51065 | .313831 | 2.38512 |
| 4 | 8.36883 | 3.34753 | .418441 | 3.18016 |
| 5 | 10.461 | 4.18441 | .523052 | 3.97519 |
| 6 | 12.5532 | 5.0213 | .627662 | 4.77023 |
| 7 | 14.6455 | 5.85818 | .732273 | 5.56527 |

DATA TABLE I-continued

| READING IN MM | VOLUME | TOTAL SOLIDS | EXTRANEOUS SOLIDS | DRC % |
|---|---|---|---|---|
| 8 | 16.7377 | 6.69506 | .836883 | 6.36031 |
| 9 | 18.8299 | 7.53195 | .941493 | 7.15535 |
| 10 | 20.9221 | 8.36883 | 1.0461 | 7.95039 |
| 11 | 23.0143 | 9.20571 | 1.15071 | 8.74543 |
| 12 | 25.1065 | 10.0426 | 1.25532 | 9.54047 |
| 13 | 27.1987 | 10.8795 | 1.35993 | 10.3355 |
| 14 | 29.2909 | 11.7164 | 1.46455 | 11.1305 |
| 15 | 31.3831 | 12.5532 | 1.56916 | 11.9256 |
| 16 | 33.4753 | 13.3901 | 1.67377 | 12.7206 |
| 17 | 35.5675 | 14.227 | 1.77838 | 13.5157 |
| 18 | 37.6597 | 15.0639 | 1.88299 | 14.3107 |
| 19 | 39.7519 | 15.9008 | 1.9876 | 15.1057 |
| 20 | 41.8441 | 16.7377 | 2.09221 | 15.9008 |
| 21 | 43.9364 | 17.5745 | 2.19682 | 16.6958 |
| 22 | 46.0286 | 18.4114 | 2.30143 | 17.4909 |
| 23 | 48.1208 | 19.2483 | 2.40604 | 18.2859 |
| 24 | 50.213 | 20.0852 | 2.51065 | 19.0809 |
| 25 | 52.3052 | 20.9221 | 2.61526 | 19.876 |
| 26 | 54.3974 | 21.759 | 2.71987 | 2.671 |
| 27 | 56.4896 | 22.5958 | 2.82448 | 21.466 |
| 28 | 58.5818 | 23.4327 | 2.92909 | 22.2611 |
| 29 | 60.674 | 24.2696 | 3.0337 | 23.0561 |
| 30 | 62.7662 | 25.1065 | 3.13831 | 23.8512 |
| 31 | 64.8584 | 25.9434 | 3.24292 | 24.6462 |
| 32 | 66.9506 | 26.7803 | 3.34753 | 25.4412 |
| 33 | 69.0428 | 27.6171 | 3.45214 | 26.2363 |
| 34 | 71.135 | 28.454 | 3.55675 | 27.0313 |
| 35 | 73.2273 | 29.2909 | 3.66136 | 27.9264 |
| 36 | 75.3195 | 30.1278 | 3.76597 | 28.6244 |
| 37 | 77.4117 | 30.9647 | 3.87058 | 29.4164 |
| 38 | 79.5039 | 31.8016 | 3.97519 | 30.2115 |
| 39 | 81.5961 | 32.6384 | 4.0798 | 31.0065 |
| 40 | 83.6883 | 33.4753 | 4.18441 | 31.8016 |
| 41 | 85.7805 | 34.3122 | 4.28902 | 32.5966 |
| 42 | 87.8727 | 35.1491 | 4.39364 | 33.3916 |
| 43 | 89.9649 | 35.986 | 4.49825 | 34.1867 |
| 44 | 92.0571 | 36.8228 | 4.60286 | 34.9817 |
| 45 | 94.1493 | 37.6597 | 4.70747 | 35.7767 |
| 46 | 96.2415 | 38.4966 | 4.81208 | 36.5718 |
| 47 | 98.3337 | 39.3335 | 4.91669 | 37.3668 |
| 48 | 100.426 | 40.1704 | 5.0213 | 38.1619 |
| 49 | 102.518 | 41.0073 | 5.12591 | 38.9569 |
| 50 | 104.61 | 41.8441 | 5.23032 | 39.7519 |
| 51 | 106.703 | 42.681 | 5.33513 | 40.547 |
| 52 | 108.795 | 13.5179 | 5.13974 | 11.342 |
| 53 | 110.887 | 44.3519 | 5.54135 | 12.1371 |
| 54 | 112.979 | 45.1917 | 5.61896 | 12.9321 |
| 55 | 115.071 | 46.0286 | 5.75357 | 43.7271 |
| 56 | 117.164 | 46.8654 | 5.85818 | 44.5222 |
| 57 | 119.256 | 47.7023 | 5.96279 | 45.3172 |
| 58 | 121.348 | 48.3392 | 6.0674 | 46.1122 |
| 59 | 123.44 | 49.3761 | 6.17201 | 46.9073 |
| 60 | 125.532 | 50.213 | 6.27662 | 47.7023 |
| 61 | 127.625 | 51.0499 | 6.38123 | 48.4974 |
| 62 | 129.717 | 51.8867 | 6.48584 | 49.2924 |
| 63 | 131.809 | 52.7236 | 6.59015 | 50.0874 |
| 64 | 133.901 | 53.5605 | 6.69506 | 50.8825 |
| 65 | 135.993 | 54.3974 | 6.79967 | 51.6775 |
| 66 | 138.086 | 55.2343 | 6.90428 | 52.4726 |
| 67 | 140.178 | 56.0712 | 7.00889 | 53.2676 |
| 68 | 142.27 | 56.908 | 7.1135 | 54.0626 |
| 69 | 144.362 | 57.7449 | 7.21812 | 54.8377 |
| 70 | 146.455 | 58.5818 | 7.32273 | 55.6527 |
| 71 | 148.547 | 59.4187 | 7.42734 | 56.4478 |
| 72 | 150.639 | 60.2556 | 7.53195 | 57.2428 |
| 73 | 152.731 | 61.0925 | 7.63656 | 58.0378 |
| 74 | 154.823 | 61.9293 | 7.74117 | 58.8329 |
| 75 | 156.916 | 62.7662 | 7.84578 | 59.6279 |
| 76 | 159.008 | 63.6031 | 7.95039 | 60.4229 |
| 77 | 161.1 | 64.44 | 8.055 | 61.218 |
| 78 | 163.192 | 65.2769 | 8.15961 | 62.013 |
| 79 | 165.284 | 66.1138 | 8.26422 | 62.8081 |
| 80 | 167.377 | 66.9506 | 8.36883 | 63.6031 |
| 81 | 169.469 | 67.7875 | 8.47344 | 64.3981 |
| 82 | 171.561 | 68.6244 | 8.57805 | 65.1932 |
| 83 | 173.653 | 69.4613 | 8.68266 | 65.9882 |
| 84 | 175.745 | 70.2982 | 8.78727 | 66.7833 |
| 85 | 177.838 | 71.135 | 8.89188 | 67.5783 |
| 86 | 179.93 | 71.9719 | 8.99649 | 68.3733 |
| 87 | 182.022 | 72.8088 | 9.1011 | 69.1684 |
| 88 | 184.114 | 73.6457 | 9.20571 | 69.9634 |
| 89 | 186.206 | 74.4826 | 9.31032 | 70.7585 |
| 90 | 188.299 | 75.3195 | 9.41493 | 71.5535 |
| 91 | 190.391 | 76.1563 | 9.51954 | 72.3485 |
| 92 | 192.483 | 76.9932 | 9.62415 | 73.1436 |
| 93 | 194.575 | 77.8301 | 9.72876 | 73.9386 |
| 94 | 196.667 | 78.667 | 9.83337 | 74.7336 |
| 95 | 198.76 | 79.5039 | 9.93798 | 75.5287 |
| 96 | 200.852 | 80.3408 | 10.0426 | 76.3237 |
| 97 | 202.944 | 81.1776 | 10.1472 | 77.1188 |
| 98 | 205.036 | 82.0145 | 10.2518 | 77.9138 |
| 99 | 207.129 | 82.8514 | 10.3564 | 78.7088 |
| 100 | 209.221 | 83.6883 | 10.461 | 79.5039 |

SUGGESTED TEST EQUIPMENT

I. DRC Micro-sample Caliper Instrument:
  Allows for agitation/coagulation of a fixed sample (0.5L) 250 ml coagulation solution and 250 ml of latex.
  Liquid is extracted by compression filtration and the solid content measured between 20 and 50% of the final volume of 250 ml latex, on a fixed expanded scale 14.

II. Disposable Micro-filters:
  Standard millipore filters 22 provide for liquid extraction and retention of solids.

III. Coagulation-Acid solution:
  An organic acid solution for floc precipitation of latex is initialized, so as to prevent entrapment of non-compressible liquid fractions.

IV. Laminated DRC Chart (Data Table I):
  Data is read directly from chart and excessive volume of DRC or adulteration will be immediately noticed, since this is reflected as a percent of extraneous solids based on the 250 ml sample volume being 100% of the total.

V. Field Test Kit—optional:
  A rapid detection method (not described) may utilize color change to indicate excessive presence of adulterants.

SAMPLE ANALYSIS:

Computational Data of Instrumentation:
Measured Volume of Cylinder = 500 ml = 0.5L ± 0.05%
Diameter (ID) = 5.161 cm
Radius = 2.580 cm
Volume per linear mm = 2.0922 ml/mm
Length of Measured Volume = 23.89 cm
Volume as a percentage per ml volume = 0.0083, 83%

A sample of raw latex is subjected to analysis by mixing in the compression cylinder with 250 ml of acid-coagulation solution. The exact measured volume of latex is obtained by a "Teflon"-coated steel beaker. The beaker is filled and leveled by spatula, leaving 250 ml ± 0.005%. The instrument handle is turned until compression stops, leaving the indicator at the 42 mm mark on the sleeve.

Since 42 mm × 2.09222 ml/mm = 87.8732 cc solids (total) and if 5% (IS) extraneous solids then 5% = 4.39364 cc. 87.8732 − 4.39364 = 83.47906 cc/250 cc = 0.333916 THEREFORE: 0.333916 × 100 = 33.3916 percent DRC 1. Obtained reading is 42 mm
2. Find 42 mm on Data Table Find reading of DRC across from 42 mm under DRC 4. Note extraneous solids=4.39364 cc of total.

I claim:

1. A volumetric analysis device for determining the solids content of a liquid composition comprising:
   A. An elongated cylinder, having a removable filter cap positioned at one end;
   B. A compression plunger mounted upon one end of an axial shaft reciprocably positioned within said cylinder, so as to compress a liquid batch contained within said cylinder, while urging liquid residue through said filter cap;
   C. A handle connected to a portion of said shaft extending through the other end of said cylinder;
   D. A reference scale positioned upon the exterior of said cylinder;
   E. An open-ended cylindrical dial drum connected to that portion of said shaft extending through said cylinder, such that reciprocal movement of said axial shaft and plunger within said cylinder is reflected correspondingly in reciprocal movement of said dial drum with respect to said reference scale upon the exterior of said cylinder.

2. A volumetric analysis device as in claim 1, said filter cap including a replaceable filter element, exposed to the interior of said cylinder.

3. A volumetric analysis device as in claim 2, said plunger being made of a resilient plastic.

4. A volumetric analysis device as in claim 3, said shaft including a clutch mechanism, translating overriding axial pressure upon said shaft to rotational movement of said dial drum with respect to said reference scale, as said plunger has compressed solid matter to a preset degree.

5. A volumetric analysis device as in claim 4, including a felt dust shield interposed between said clutch mechanism and said dial drum.

6. A volumetric analysis device as in claim 5, said clutch mechanism including a plurality of shaft pads and drive plates encircling said axial shaft in alternate array, said shaft pads being keyed to said shaft and said drive plates complementally engaging peripheral recesses in the inner wall of said clutch mechanism.

7. A volumetric analysis device as in claim 6, said dial drum being open-ended adjacent said removable filter cap and being substantially coextensive with said cylinder in the plunger compressed position.

8. A volumetric analysis device for determining the dry rubber content of a latex solution comprising:
   A. An elongated cylinder, having a removable filter cap positioned at one end;
   B. A compression plunger mounted upon one end of an axial shaft reciprocably positioned within said cylinder, so as to compress a liquid batch contained within said cylinder, while urging liquid residue through said filter cap;
   C. A handle connected to a portion of said shaft extending through the other end of said cylinder;
   D. A reference scale positioned upon the exterior of said cylinder;
   E. An open-ended cylindrical dial drum connected to that portion of said shaft extending through said cylinder, such that reciprocal movement of said axial shaft and plunger within said cylinder is reflected correspondingly in reciprocal movement of said dial drum with respect to said reference scale upon the exterior of said cylinder.

* * * * *